United States Patent [19]
Hay et al.

[11] Patent Number: 6,103,913
[45] Date of Patent: Aug. 15, 2000

[54] PROCESS FOR PREPARING ENOLLACTONE DERIVATIVES

[75] Inventors: David Allen Hay; Tony Yantao Zhang, both of Indianapolis, Ind.

[73] Assignees: Eli Lilly and Company, Indianapolis, Ind.; Wayne State University, Detroit, Mich.; University of Hawaii, Honolulu, Hi.

[21] Appl. No.: 09/374,953

[22] Filed: Aug. 16, 1999

Related U.S. Application Data

[60] Provisional application No. 60/104,645, Oct. 16, 1998.

[51] Int. Cl.[7] .................................................. C07D 309/30
[52] U.S. Cl. ........................... 549/292; 549/60; 548/517; 546/282.1
[58] Field of Search .................. 549/292, 61; 546/282.1; 548/517

[56] References Cited

U.S. PATENT DOCUMENTS

| | | | |
|---|---|---|---|
| 4,845,085 | 7/1989 | Sesin | 31/395 |
| 4,845,086 | 7/1989 | Sesin | 31/395 |
| 4,868,208 | 9/1989 | Sesin et al. | 514/475 |
| 4,946,835 | 8/1990 | Hirsch et al. | 514/183 |

FOREIGN PATENT DOCUMENTS

| | | | |
|---|---|---|---|
| WO 95/17093 | 12/1994 | WIPO | A01N 37/18 |
| WO 96/40184 | 3/1996 | WIPO | A61K 38/00 |
| WO 96/39829 | 6/1996 | WIPO | A01N 37/18 |
| WO 97/07798 | 8/1996 | WIPO | A61K 31/395 |
| WO 97/08334 | 8/1996 | WIPO | C12P 21/04 |
| WO 97/23211 | 12/1996 | WIPO | A61K 31/395 |
| WO 98/08505 | 8/1997 | WIPO | A61K 31/395 |
| WO 98/08506 | 8/1997 | WIPO | A61K 31/395 |
| WO 98/08829 | 8/1997 | WIPO | C07D 273/08 |

OTHER PUBLICATIONS

Russell A. Barrow, et al., Total Synthesis of Cryptophycins. Revision of the Structures of Cryptophycins A and C. *J. Am. Chem. Soc.* (1995), 117, 2479–2490.

Robert E. Schwartz, et al. Pharmaceuticals from Cultured Algae. *Journal of Industrial Microbiology*, 5 (1990) 113–123.

Motomasa Kobayashi, et al. A total synthesis of Arenastatin A, an extremely potent cyctotoxic eepsipeptide, from the Okinawan marine sponge Dysidea Arenaria, *Chem. Pharm. Bull.* (1994) 42(11); 2394–2396.

Charles D. Smith, et al., Cryptophycin: A New Antimicrotubule Agent Active Against Drug–Resistant Cells. *Cancer Research* 54, 3779–3784, Jul. 15, 1994.

Golakoti Trimurtulu, et al., Total Structures of Cryptophycins, Potent Antitumor Depsipeptides from the Blue–Green Alga *Nostoc Sp.* Strain GSV 224. *J. Am. Chem. Soc.* 1994, 116, 4729–4737.

Kristen Kerksiek, et al., Interaction of Cryptophycin 1 with Tubulin and Microtubules. *FEBS Letters* 377 (1995) 59–61.

Motomasa Kobayashi, et al. Improved Total Synthesis and Structure–Activity Relationship of Arenastatin A, A Potent Cytotoxic Spongean Depsipeptide. *Chem. Pharm. Bull* 43(9) 1598–1600 (1995).

Trimurtulu Golakoti, et al. Structure Determination, Conformational Analysis, Chemical Stability Studies, and Antitumor Evaluation of the Cryptophycins. Isolation of 18 New Analogs from *Nostoc Sp.* Strain GSV 224. *J. Am. Chem. Soc.*, 1995, 117, 12030–12049.

Ruoli Bai, et al. Characterization of the Interaction of Cryptophycin 1 with Tubulin: Binding in the Vinca Domain, Competitive Inhibition of Dolastatin 10 Binding, and an Unusual Aggregation Reaction. *Cancer Research* 56, 4398–4406, Oct. 1, 1996.

Charles D. Smith, et al. Mechanism of Action of Cryptophycin. *Journal of Biological Chemistry*, vol. 271, No. 11, Mar. 15, 1996, pp. 6192–6198.

Gregorz M. Salamonczyk, et al. Total Synthesis of Cryptophycins via a Chemoenzymatic Approach. *J. Org. Chem.*, 1996, 61, 6893–6900.

Rabindra Rej, et al. total synthesis of cryptophycins and their 16–(3–phenylacryloyl) derivatives. *J. Org. Chem.* 1996, 61, 6289–6295.

Richard E. Moore, et al. The Search for New Antitumor Drugs from Blue–Green Algae. *Current Pharmaceutical Design*, 1996, 2, 317–330.

T.H. Corbett, et al. Preclinical Anticancer Activity of Cryptophycin–8. *Journal of Experimental Therapeutics and Oncology*, vol. 1, No. 2, Mar. 1996, pp. 95–108.

Dulal Panda, et al. Mechanism of Action of the Unusually Potent Microtubule Inhibitor Cryptophycin 1. *Biochemistry* 1997, 36, 12948–12953.

Kevin M. Gardinier, et al. Enantiospecific Total Synthesis of the Potent Antitumor Macrolides Cryptophycins 1 and 8. *J. Org. Chem.* 1997, 62, 7098–7099.

Syed M. Ali, et al. Formal Syntheses of Cryptophycin A and Arenastatin A. *Tetrahedron Letters*, vol. 38, No. 10, pp. 1703–1706, 1997.

Gottunukkala V. Subbaraju, et al., Three New Cryptophycins from *Nostoc Sp.* GSV 224, *J. Nat. Prod.*, 1997, 60, 302–305.

*Primary Examiner*—Amelia Owens
*Attorney, Agent, or Firm*—John H. Engelmann

[57] ABSTRACT

This invention provides processes for preparing lactone intermediates useful for the preparation of pharmaceutical compounds such as tetrahydrolipstatin and cryptophycin compounds.

18 Claims, No Drawings

PROCESS FOR PREPARING ENOLLACTONE DERIVATIVES

CROSS-REFERENCE

This application claims the benefit of U.S. Provisional Application No. 60/104,645, filed Oct. 16, 1998.

BACKGROUND OF THE INVENTION

This invention relates to the fields of pharmaceutical and organic chemistry and provides a new process for preparing intermediates useful for the preparation of cryptophycin compounds.

An efficient totally synthetic process for the preparation of useful cryptophycin compounds is desired for commercial production of such cryptophycin compounds which have been found to have antimicrotubulin properties.

The processes claimed herein provide important elements needed for an efficient total synthetic route for preparing useful cryptophycin compounds and intermediates. 4-Hydroxy-5,6-dihydropyran-2-one and derivatives thereof are important intermediates for a number of natural products; D. Seebach et al., *Angew. Chem. Int. Ed.* 13, 77 (1974); R. M. Carlson et al., *J. Org. Chem.* 40, 1610 (1975). Additionally, this series of compounds has been used for the synthesis of pharmaceuticals, for example, the drug tetrahydrolipstatin ("THL"); J. J. Landi, Jr. et al., *Tetrahedron Lett.*, 34, 277 (1993); U.S. Pat. No. 4,598,089. Current art teaches that in order to form a carbon—carbon bond at the terminal (4-) position of an acylacetate, two equivalents of strong base, for example sodium hydride or n-butyl lithium, in an aprotic solvent must be used to deprotonate both the 2- and 4- positions, proceeding through selective alkylation of a dianion with one equivalent of electrophiles; S. M. Huckin et al., *Can. J. Chem.* 52, 2157 (1974); S. M. Huckin et al., *J. Am. Chem. Soc.* 96, 1082 (1974); N. Petragnani et al., *Synthesis*, 521, 78 (1982); J. R. Peterson et al., *Syn. Commun.* 18, 949 (1988); D. Seebach et al., *Angew. Chem.* 86, 40 (1974); H. Kashihara et al., *Chem. Pharm. Bull.* 34, 4527 (1986).

However, even under such harsh conditions, paraformaldehyde or formaldehyde have been poor electrophiles and product yield has been low. In fact, a toxic reagent, $PhCH_2OCH_2Cl$ has been used instead of paraformaldehyde for this purpose in a multistep synthesis; E. C. Taylor et al., *J. Org. Chem.* 50, 5223 (1985).

The present invention provides a novel process for the preparation of lactone derivatives in high yield using simple aldehydes or ketones and less than two equivalents of base and more than one equvalent of aldehyde.

The present invention further provides novel intermediates useful in the preparation of cryptophycin compounds or other pharmaceutical agents, such as THL.

SUMMARY OF THE INVENTION

The present invention provides a novel process for preparing a compound of the formula

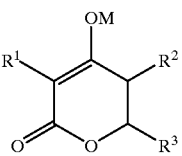

(I)

wherein $R^1$, $R^2$ and $R^3$ are each independently $C_1$–$C_{12}$ alkyl, aryl or heteroaryl and M is hydrogen or a cation; or a pharmaceutically acceptable salt thereof;
comprising reacting an acylacetate of formula

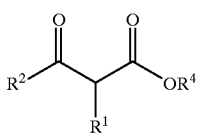

(1)

wherein $R^1$ and $R^2$ are as defined above and $R^4$ is $C_1$–$C_{12}$ alkyl, aryl or heteroaryl; with from about 1.0 to about 2.0 molar equivalents of a suitable base; and an aldehyde of the formula $$R^3C(O)H \tag{3}$$

wherein $R^3$ is as defined as above; or a ketone of the formula $$R^5C(O)R^5 \tag{4}$$

wherein $R^3$ is as defined above and $R^5$ is $C_1$–$C_{12}$ alkyl, aryl or heteroaryl; to yield a compound of formula (I); and optionally forming a pharmaceutically acceptable salt thereof.

The invention further provides a process for preparing a compound of the formula

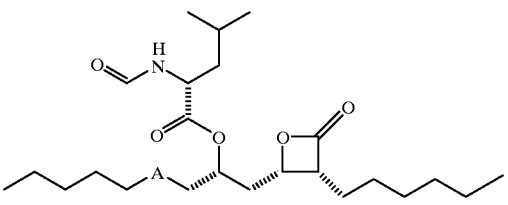

(II)

wherein A signifies the group

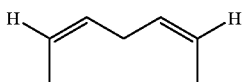

or $—(CH_2)_5—$; said process comprising the steps of
(a) reacting an acylacetate of formula

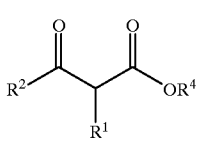

(1)

wherein $R^1$ and $R^2$ are as defined above and $R^4$ is $C_1$–$C_{12}$ alkyl, aryl or heteroaryl; with from about 1.0 to about 2.0 molar equivalents of a suitable base; and an aldehyde of the formula $$R^3C(O)H \quad (3)$$

wherein $R^3$ is as defined as above; or a ketone of the formula $$R^5C(O)R^5 \quad (4)$$

wherein $R^3$ is as defined above and $R^5$ is $C_1$–$C_{12}$ alkyl, aryl or heteroaryl; to yield a compound of the formula

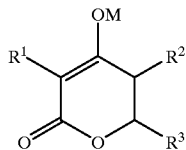

(I)

wherein $R^1$, $R^2$ and $R^3$ are as defined above and M is hydrogen or a cation; and (b) converting the compound of formula (I) to a compound of formula (II) and optionally forming a pharmaceutically acceptable salt thereof.

The invention further provides novel intermediates of formula (III)

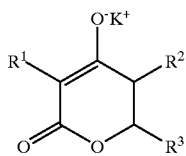

(III)

wherein $R^1$, $R^2$ and $R^3$ are as defined above; useful in the preparation of THL.

DETAILED DESCRIPTION OF THE INVENTION

As used herein, the term "pharmaceutically acceptable salt" refers to either acid addition salts or base addition salts.

The expression "pharmaceutically acceptable acid addition salt" is intended to apply to any non-toxic organic or inorganic acid addition salt of the compounds of formula I or any of its intermediates. Illustrative inorganic acids which form suitable salts include hydrochloric, hydrobromic, sulphuric, and phosphoric acid and acid metal salts such as sodium monohydrogen orthophophate, and potassium hydrogen sulfate. Illustrative organic acids which form suitable salts include the mono-, di- and tricaboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy-benzoic, and sulfonic acids such as p-toluenesulfonic acid, methane sulfonic acid and 2-hydroxyethane sulfonic acid. Such salts can exist in either hydrated or substantially anhydrous form.

The expression "pharmaceutically acceptable basic addition salts" is intended to apply to any non-toxic organic or inorganic basic addition salts of the compounds of formula I or any of its intermediates. Illustrative bases which form suitable salts include alkali metal or alkaline-earth metal hydroxides such as sodium, potassium, calcium, magnesium or barium hydroxides; ammonia and aliphatic, cyclic or aromatic organic amines such as methylamine, dimethylamine, trimethylamine, diethylamine, triethylamine, isopropyldiethylamine, pyridine and picoline.

As used herein, the term "$C_1$–$C_{12}$ alkyl" refers to a saturated straight or branched chain hydrocarbon radical of from one to twelve carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl, heptyl, octyl, 2-methylheptyl, nonyl, decyl, and the like. Included within the term is the term "$C_1$–$C_6$ alkyl" which refers to a saturated straight or branched chain hydrocarbon radical of from one to six carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl, and the like. Also included within this term is the term "$C_1$–$C_4$ alkyl" which refers to a saturated straight or branched chain hydrocarbon radical of from one to four carbon atoms. Included within the scope of this term are methyl, ethyl, n-propyl, isopropyl, n-butyl, isobutyl, sec-butyl, tert-butyl and the like.

The term "aryl" refers to an aromatic radical of from 6 to 12 carbon atoms, such as phenyl or naphthyl groups wherein said groups are optionally substituted with one, two or three substituents selected from the group consisting of $C_1$–$C_4$ alkyl, halo-substituted $C_1$–$C_4$ alkyl, halogen or $C_1$–$C_4$ alkoxy. The terms "lower alkoxyl group" or "$C_1$–$C_5$ alkoxy" refers to an alkyloxy radical made up of an oxygen radical bearing a saturated straight or branched chain hydrocarbyl radical of one to five carbon atoms and specifically includes methoxy, ethoxy, propyloxy, isopropyloxy, n-butyloxy, isobutyloxy, sec-butyloxy, tertiary butyloxy, pentyloxy and the like. Specifically included with the scope of the term "aryl" are phenyl, p-toluoyl, p-methoxyphenyl, p-chlorophenyl, naphthyl and the like.

As used herein, the term "heteroaryl" refers to a substituted or unsubstituted heteroaromatic radical which contains one or more non-carbon substituents within the ring, said substituents selected from oxygen, nitrogen or sulfur. The total number of carbon atoms and non-carbon atoms in the ring range from four to twelve atoms. Specifically included with the scope of the term "heteroaryl" are monocyclic conjugated systems such as furyl, pyrrolyl, thienyl, pyridyl, and the like and bicyclic conjugated systems such as indole.

As used herein, the term "cation" refers to a positively charged ion. Depending on the suitable base used in the process for forming the lactones of the present invention, suitable cations include potassium, sodium, cesium, tetrabutylammonium, and the like.

The acylacetates of formula (II) are known or readily prepared by one of ordinary skill in the art. Examples include ethyl 2-methylacetoacetate, ethyl 2-n-hexylacetoacetate, ethyl 2-ethylacetoacetate, ethyl 2-n-propylacetoacetate, ethyl 2-isopropylacetoacetate, and the like.

Suitable bases used to react with the acylacetates of formula (II) are any organic or inorganic bases capable of abstracting a proton from the 2-position of the acylacetate of formula (II). Examples include potassium t-butoxide; sodium hydride and lithium dialkylamides, for example, lithium diisopropylamide; and the like. Most preferred is potassium t-butoxide.

The suitable base is dissolved in an organic solvent, for example, an alcoholic solvent, such as methanol, ethanol, 2-propanol, and the like, or mixtures thereof; tetrahydrofuran, and the like. Most preferred are alcoholic solvents, such as 2-propanol. The amount of suitable base to be dissolved ranges from about 1.0 molar equivalents to about 2.0 molar equivalents as compared to the acylacetate of formula (2). Preferably, the amount of suitable base ranges from about 1.3 to about 1.7 molar equivalents. Most preferably, the amount of suitable base ranges from about 1.4 to about 1.6 molar equivalents.

The basic solution is cooled to a temperature ranging from about −30° C. to about 30° C., preferably under an inert atmosphere, such as nitrogen, in preparation for the reaction with the desired acylacetate of formula (2). Most preferably, the solution is cooled to about 0° C.

The acylacetate of formula (2) is added to the basic solution at a rate so as to maintain the temperature at or below +10° C. Preferably, the acylacetate of formula (II) is added so as to maintain the temperature between −5° C. and +7° C. Most preferably, the acylacetate of formula (II) is added so as to maintain the temperature between 0° C. and +5° C.

The acylacetate basic solution is then reacted with a suitable aldehyde of formula (3) or ketone of formula (4). The amount of aldehyde of formula (3) or ketone of formula (4) to be added ranges from about 1.0 molar equivalents to about 3.0 molar equivalents as compared to the acylacetate of formula (2). Preferably, the amount of suitable base ranges from about 1.1 to about 2.2 molar equivalents. Most preferably, the amount of suitable base ranges from about 1.2 to about 1.5 molar equivalents. Generally, the aldehyde of formula (3) or ketone of formula (4) is reacted with the acylacetate solution at a temperature ranging from about 0° C. to about 50° C. Most preferably, the reaction is carried out at room temperature.

The resulting mixture is then acidified with a suitable acid, such as hydrochloric acid. The acidified mixture is then isolated and purified according to methods appreciated by one of ordinary skill in the art, such as extraction, evaporation, filtration and recrystallization to provide the lactone of formula (3).

The preferred aldehydes of formula (3) or ketones of formula (4) include paraformaldehyde, acetaldehyde, acetone, and the like.

A general synthetic method for synthesizing a compound of formula (II) is set forth in U.S. Pat. No. 4,598,098, issued Jul. 1, 1986; herein incorporated by reference as if fully set forth. General synthetic methods of synthesizing a compound of formula (II) using a compound of formula (I) include European Patent Application OPI No. 0524495A1, published Jul. 9, 1993; and P. Barbier et al., *J. Org. Chem.* 53, 1218–1221 (1988). Other methods of synthesizing a compound of formula (II) include P. Barbier et al., *Helv. Chim. Acta* 70(5), 1412–1418 (1987); and P. Barbier et al., *Helv. Chim. Acta* 70(1), 196–202 (1987).

General synthetic processes for synthesizing cryptophycin compounds are disclosed in Barrow, R. A. et al., *J. Am. Chem. Soc.* 117, 2479 (1995); PCT Intnl. Publ. No. WO 96/40184, published Dec. 19, 1996; PCT Intnl. Publ. No. WO 98/08505, published Mar. 5, 1998; PCT Intnl. Publ. No. WO 97/07798, published Mar. 6, 1998; PCT Intnl. Publ. No. WO 97/23211, published Jul. 3, 1997; PCT Intnl. Publ. No. WO 98/08506, published Mar. 5, 1998; PCT Intnl. Publ. No. WO 98/08812, published Mar. 5, 1998; and PCT Intnl. Publ. No. WO 97/31632, published Sep. 4, 1997. References disclosing intermediates and/or processes for preparing cryptophycin compounds or intermediates thereof include PCT Intnl. Publ. No. WO 98/09955, published Mar. 12, 1998; PCT Intnl. Publ. No. WO 98/09974, published Mar. 12, 1998; PCT Intnl. Publ. No. WO 98/09601, published Mar. 12, 1998; and PCT Intnl. Publ. No. WO 98/09988, published Mar. 12, 1998.

Optionally, on those compounds of formula (I), (II) or (III) containing basic or acidic functional groups, pharmaceutically acceptable salts of the compounds of formulae (I), (II) or (III) may be formed using standard techniques. For example, the free base may be dissolved in aqueous or aqueous-alcohol solution or other suitable solvent containing the appropriate acid and the salt isolated by evaporating the solution. Alternatively, the free base may be reacted in an organic solvent containing the appropriate acid and the salt isolated by evaporating the solution. Further, the free base may be reacted in an organic solvent in which case the salt separates directly or can be obtained by concentration of the solution or in a solvent such as water which is then removed in vacuo or by freeze-drying, or by exchanging the cations of an existing salt for another cation on a suitable ion exchange resin.

Preferred embodiments of formula (I) and (III) are given below:

(i) $R^1$ is $C_1$–$C_6$ alkyl; most preferably methyl.

(ii) $R^2$ is hydrogen or $C_1$–$C_6$ alkyl; most preferably hydrogen.

(iii) $R^3$ is hydrogen, $C_1$–$C_6$ alkyl or phenyl; most preferably hydrogen, methyl or phenyl.

(iv) M is hydrogen or potassium;

(v) The combination of embodiments (i)–(iv).

To further illustrate the invention the following examples are provided. The scope of the invention is in no way to be construed as limited to or by the following examples. The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" or "mL" means milliliter or milliliters; "M" refers to molar or molarity; "MS" refers to mass spectrometry; "IR" refers to infrared spectroscopy; and "NMR" refers to nuclear magnetic resonance spectroscopy.

EXAMPLE 1

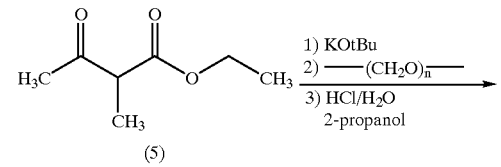

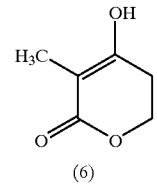

5,6-Dihydro-4-hydroxy-3-methyl-2H-pyran-2-one
(6)

A solution of potassium t-butoxide (11.2 g, 100 mmol) was prepared in 2-propanol (160 mL), stirred, and cooled to 0° C. under nitrogen. This mixture was treated with ethyl 2-methylacetoacetate (5, 12.0 g, 83.2 mmol), dropwise, and at such a rate as to keep the temperature at or below +5° C. (approximately 10 min.). After stirring for 20 min at 0° C., the resulting slurry was treated with paraformaldehyde (6.00 g, 200 mmol), in one portion, the ice bath was removed, and the suspension was stirred at room temperature for 90 min. The resulting cloudy yellow mixture was evaporated and the residue partitioned between ice water and TBME. The layers were separated and the aqueous layer was diluted with tetrahydrofuran (150 mL), cooled to 0° C., and acidified with HCl (conc., 10 mL, 120 mmol). After stirring for 30 min, the mixture was treated with NaCl (20 g), the layers were separated, and the aqueous layer was extracted with tetrahydrofuran (150 mL). The organic layers were dried (MgSO$_4$), filtered, and the filtrate evaporated. The residue was stirred with EtOAc (100 mL) at 0° C. for 30 min and filtered to provide 5,6-dihydro-4-hydroxy-3-methyl-2H-pyran-2-one (6) as a snow white powder (5.90 g, 55% yield): mp 138–144° C. (d); IR (KBr): $\upsilon_{max}$ 3421, 1631 cm$^{-1}$; $^1$H NMR (DMSO-d$_6$) δ10.6 (1 H, bs), 4.18 (2 H, t, J=6.4 Hz), 2.53 (2 H, t, J=6.4 Hz), 1.63 (3 H, s); MS (FIA), m/z 129.1 (M+1)$^+$.

EXAMPLE 2

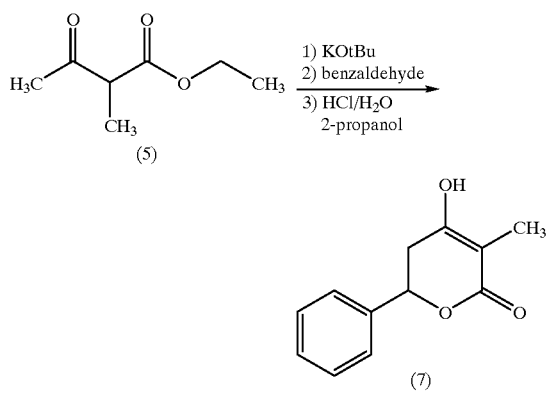

5,6-Dihydro-4-hydroxy-3-methyl-5-phenyl-2H-pyran-2-one (7)

A solution of potassium t-butoxide (2.80 g, 22.9 mmol) was prepared in 2-propanol (40 mL), stirred, and cooled to 0° C. under nitrogen. This mixture was treated with ethyl 2-methylacetoacetate (5, 3.00 g, 20.8 mmol), dropwise, and at such a rate as to keep the temperature at or below +5° C. (approximately 10 min.). After stirring for 20 min at 0° C., the resulting slurry was treated with benzaldehyde (2.80 g, 22.9 mmol), in one portion, the ice bath was removed, and the suspension was stirred at room temperature for 90 min. The mixture was again cooled to 0° C. and acidified with HCl (conc., 2.0 mL, 24 mmol in 5 mL water). After stirring overnight at room temperature, the mixture was poured into water (150 mL) and extracted with tetrahydrofuran/ether (1/1, 2×100 mL). The organic layers were dried (MgSO$_4$), filtered, and the filtrate evaporated. The residue was stirred in EtOAc (100 mL) at 0° C. for 30 min and filtered to provide 5,6-dihydro-4-hydroxy-3-methyl-5-phenyl-2H-pyran-2-one (7) as a snow white powder (2.62 g, 62% yield): mp 190–191° C. (d). Anal. Calcd for C$_{12}$H$_{12}$O$_3$ (204.23): C, 70.58; H, 5.92. Found: C, 70.45; H, 6.03. IR (KBr): $\upsilon_{max}$ 2640, 1605 cm$^{-1}$; $^1$H NMR (DMSO-d$_6$) δ10.8 (1 H, bs), 7.4 (5 H, m), 5.43 (1 H, dd, J=11, 3.9 Hz), 2.83 (1 H, dd, J=17, 11 Hz), 2.62 (1 H, dd, J=17, 3.9 Hz), 1.69 (3 H, s); MS (FIA), m/z 205.1 (M+1)$^+$.

EXAMPLE 3

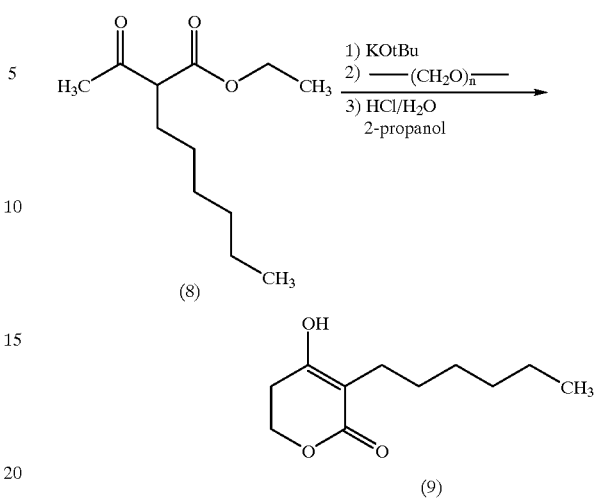

5,6-Dihydro-3-n-hexyl-4-hydroxy-2H-pyran-2-one (9)

A solution of potassium t-butoxide (0.69 g, 5.65 mmol) was prepared in 2-propanol (9 mL), stirred, and cooled to 0° C. under nitrogen. This mixture was treated with ethyl 2-n-hexylacetoacetate (8, 1.00 g, 4.67 mmol), dropwise, and at such a rate as to keep the temperature at or below +6° C. (approximately 5 min.). After stirring for 20 min at 0° C., the resulting slurry was treated with paraformaldehyde (0.34 g, 2.42 mmol), in one portion, the ice bath was removed, and the suspension was stirred at room temperature for 90 min. The mixture was cooled to 0° C. and acidified with HCl (1N, 6 mL, 6 mmol). After stirring overnight at room temperature, the mixture was concentrated and the residue partitioned between water and CH$_2$Cl$_2$, and the organic layers were dried (MgSO$_4$), filtered, and the filtrate evaporated. The resulting oil was dissolved in hexanes (10 mL), allowed to stand at 0° C. for 60 min, then filtered to provide 5,6-dihydro-3-n-hexyl-4-hydroxy-2H-pyran-2-one (9) as a snow white powder (370 mg, 40% yield): mp 98–99° C. (d). Anal. Calcd for C$_{11}$H$_{18}$O$_3$ (198.26): C, 66.64; H, 9.15. Found: C, 66.49; H, 9.14. IR (KBr): $\upsilon_{max}$ 2924, 1594, 1381 cm$^{-1}$; $^1$H NMR (DMSO-d$_6$) δ10.6 (1 H, bs), 4.16 (2 H, t, J=6.3 Hz), 2.54 (2 H, t, J=6.3 Hz), 2.15 (2 H, t, J=7.4 Hz), 1.3 (8 H, m); 0.86 (3H, t, J=6.8 Hz); MS (FIA), m/z 199.2 (M+1)$^+$.

We claim:

1. A process for preparing a compound of the formula

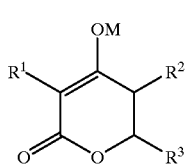

(I)

wherein R$^1$, is C$_1$–C$_{12}$ alkyl, aryl or heteroaryl, R$^2$ and R$^3$ are each independently hydrogen, C$_1$–C$_{12}$ alkyl, aryl or heteroaryl and M is hydrogen or a cation; or a pharmaceutically acceptable salt thereof;

comprising reacting an acylacetate of formula

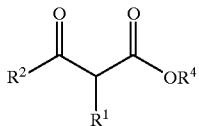

(1)

wherein $R^1$ and $R^2$ are as defined above and $R^4$ is $C_1$–$C_{12}$ alkyl, aryl or heteroaryl; with from about 1.0 to about 2.0 molar equivalents of a suitable base; and an aldehyde of the formula $R^3C(O)H$ (3)

wherein $R^3$ is as defined as above; or a ketone of the formula $R^5C(O)R^5$ (4)

wherein $R^3$ is as defined above and $R^5$ is $C_1$–$C_{12}$ alkyl, aryl or heteroaryl; to yield a compound of formula (I); and optionally forming a pharmaceutically acceptable salt thereof.

2. A process according to claim 1 wherein $R^1$ is $C_1$–$C_6$ alkyl; $R^2$ is hydrogen; $R^3$ is hydrogen; $C_1$–$C_6$ alkyl; or phenyl and M is hydrogen or potassium.

3. A process according to claim 2 wherein $R^1$ is methyl.

4. A process according to claim 1 wherein said compound of formula (I) is 5,6-Dihydro-4-hydroxy-3-methyl-2H-pyran-2-one.

5. A process according to claim 1 wherein said compound of formula (I) is 5,6-Dihydro-4-hydroxy-3-methyl-5-phenyl-2H-pyran-2-one.

6. A process according to claim 1 wherein said compound of formula (I) is 5,6-Dihydro-3-n-hexyl-4-hydroxy-2H-pyran-2-one.

7. A process according to claim 1 wherein said suitable base is potassium t-butoxide; sodium hydride or a lithium dialkylamide.

8. A process according to claim 7 wherein said suitable base is potassium t-butoxide.

9. A process according to claim 1 wherein the amount of suitable base ranges from about 1.3 to about 1.7 molar equivalents.

10. A process according to claim 1 wherein the amount of suitable base ranges from about 1.4 to about 1.6 molar equivalents.

11. A process according to claim 8 wherein the amount of suitable base ranges from about 1.4 to about 1.6 molar equivalents.

12. A process according to claim 10 further comprising dissolving said suitable base in an alcoholic solvent to form a basic solution.

13. A process according to claim 12 further comprising adding the acylacetate of formula (II) to the basic solution so as to maintain the temperature between −5° C. and +7° C.

14. A process according to claim 10 further comprising adding the aldehyde of formula (3) or the ketone of formula (4) in a range of from about 1.0 molar equivalents to about 3.0 molar equivalents as compared to the acylacetate of formula (2).

15. A process according to claim 13 further comprising adding the aldehyde of formula (3) or the ketone of formula (4) in a range of from about 1.0 molar equivalents to about 3.0 molar equivalents as compared to the acylacetate of formula (2).

16. A compound of the formula

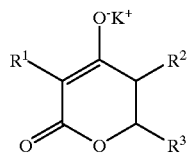

(III)

wherein $R^1$, $R^2$ and $R^3$ are each independently $C_1$–$C_{12}$ alkyl, aryl or heteroaryl.

17. A compound of claim 16 wherein $R^1$ is n-hexyl; $R^2$ is hydrogen and $R^3$ is —$(CH_2)_{10}CH_3$.

18. In a process for preparing cryptophycin molecules wherein the improvement comprises the use of Compound I, prepared by the method of claim 1, as an intermediate.

* * * * *